US00RE49502E

(19) United States
(12) Reissued Patent
Baumgartner et al.

(10) Patent Number: US RE49,502 E
(45) Date of Reissued Patent: Apr. 25, 2023

(54) PHENYL BASED COMPOUNDS SUBSTITUTED WITH ALDEHYDE MOIETIES AND THEIR USE IN PERFUMERY

(71) Applicant: GIVAUDAN SA, Vernier (CH)

(72) Inventors: Corinne Baumgartner, Faellanden (CH); Yue Zou, Jiangsu (CN)

(73) Assignee: GIVAUDAN SA, Vernier (CH)

(21) Appl. No.: 16/922,570

(22) Filed: Jul. 7, 2020

Related U.S. Patent Documents

Reissue of:
(64) Patent No.: 10,443,018
Issued: Oct. 15, 2019
Appl. No.: 15/516,810
PCT Filed: Oct. 9, 2015
PCT No.: PCT/EP2015/073374
§ 371 (c)(1),
(2) Date: Apr. 4, 2017
PCT Pub. No.: WO2016/074865
PCT Pub. Date: May 19, 2016

(30) Foreign Application Priority Data

Nov. 10, 2014 (WO) ..... PCT/CN2014/090675

(51) Int. Cl.
*C11B 9/00* (2006.01)
*C07C 47/228* (2006.01)
*C11D 3/50* (2006.01)

(52) U.S. Cl.
CPC ..... *C11B 9/0061* (2013.01); *C07C 47/228* (2013.01); *C11D 3/50* (2013.01)

(58) Field of Classification Search
CPC ... C11B 9/0061; C11B 9/0034; C07C 47/228; C11D 3/50
See application file for complete search history.

(56) References Cited

U.S. PATENT DOCUMENTS 4,113,781 A 9/1978 Aquila et al.
4,710,316 A * 12/1987 Hafner ..... C07C 29/54 512/20
4,968,668 A 11/1990 Hafner et al.
5,527,769 A 6/1996 Winter et al.
5,552,379 A 9/1996 Winter et al.
6,103,688 A 8/2000 Winter et al.
6,147,049 A * 11/2000 Gygax ..... C07C 45/86 568/309
6,313,354 B1 * 11/2001 Markert ..... C07C 45/515 568/425
8,399,399 B2 * 3/2013 Kaiser ..... C07C 47/21 510/105
9,656,938 B2 * 5/2017 Goeke ..... C07C 47/228
9,988,592 B2 * 6/2018 Goeke ..... C07C 47/228
10,047,031 B2 * 8/2018 Baumgartner ..... C11B 9/003

(Continued)

FOREIGN PATENT DOCUMENTS

CN 101605765 A 12/2009
DE 3703584 A1 8/1998

(Continued)

OTHER PUBLICATIONS

Tang et al, "N-Heterocyclic Carbene Catalyzed Reaction of 2-(2-Aroylvinyl)cinnamaldehydes with α,β-Unsaturated Imines: An Efficient Method for the Stereoselective Synthesis of Highly Functionalized Indane Derivatives," Synthesis, vol. 46, pp. 87-95, published online Nov. 6, 2013. (Year: 2013).*
JP Office Action for corresponding application JP 2017-525063 dated Jul. 1, 2019.
English summary of JP Office Action for corresponding application JP 2017-525063 dated Jul. 1, 2019.
CAS Entry No. 860390-00-7; Benzeneacetaldehyde, 2-ethyl-a, 4-dimethyl- (CA Index Name), May 27, 2019.
H. Chen, et al., "Facile synthesis of (E)—Alkenyl aldehides from allyl arenes or alkenes via Pd (II)—catalyzed direct oxygenation of allylic C-H bond", Organic Letters, American Chemical Society, vol. 13, 2011, pp. 992-994.
S.Z. Cagen, et al., "Toxicity Induced by Subchronic Dermal Exposure to Paratertiary Butyl Benzoic Acid (ptBBA) in Fischer 344 Rats", Journal of American College of Toxicology, vol. 8, No. 5, p. 1027-1038, 1989.

(Continued)

*Primary Examiner* — Alan D Diamond
*Assistant Examiner* — Jerry D Johnson
(74) *Attorney, Agent, or Firm* — Norris McLaughlin PA

(57) ABSTRACT

A compound represented by the formula 1

Formula 1

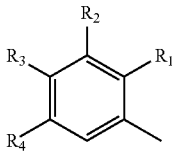

wherein $R_1$ is H, or when $R_2$ and $R_3$ is H, then $R_1$ is $CHR_5CHR_6CHO$, $CR_5{=}CR_6CHO$ or $C(CH_3)CHO$, wherein $R_5$, $R_6$ each independently may represent H or methyl;

$R_2$ is H, or when $R_1$ and $R_3$ is H, then $R_2$ is $CHR_5CHR_6CHO$, $CR_5{=}CR_6CHO$ or $C(CH_3)CHO$, wherein $R_5$, $R_6$ each independently may represent H or methyl;

$R_3$ is H, or when $R_1$ and $R_2$ is H, then $R_3$ is $CHR_5CHR_6CHO$, $CR_5{=}CR_6CHO$ or $C(CH_3)CHO$, wherein $R_5$, $R_6$ each independently may represent H or methyl; and $R_4$ is methyl or a branched or linear, saturated or unsaturated, unsubstituted or substituted (optionally with cyclopropyl groups), $C_2$-$C_7$ alkyl or alkenyl residue, preferentially isobutyl, isoamyl.

Said compounds are useful as perfume ingredients in personal care and household care products.

19 Claims, No Drawings

(56) References Cited

U.S. PATENT DOCUMENTS

| | | | | |
|---|---|---|---|---|
| 2010/0152083 | A1* | 6/2010 | Velazquez | C11D 3/50 510/103 |
| 2011/0308555 | A1 | 12/2011 | Smets et al. | |

FOREIGN PATENT DOCUMENTS

| | | | | |
|---|---|---|---|---|
| EP | 685444 | A1 | * | 12/1995 |
| GB | 988502 | | * | 4/1965 |
| GB | 1057360 | | * | 2/1967 |
| JP | H07330653 | A | | 12/1995 |
| JP | 2004513217 | A | | 4/2004 |
| JP | 2012511614 | A | | 5/2012 |
| WO | WO 99/29823 | A1 | * | 6/1999 |
| WO | 0238120 | A1 | | 5/2002 |
| WO | 2006085049 | A1 | | 8/2006 |
| WO | 2007143873 | A2 | | 12/2007 |
| WO | 2008065181 | A2 | | 6/2008 |
| WO | 2008093272 | A2 | | 8/2008 |
| WO | 2009027957 | A2 | | 3/2009 |
| WO | 2010105873 | A2 | | 9/2010 |
| WO | 2012139912 | A1 | | 10/2012 |
| WO | 2012172120 | A2 | | 12/2012 |
| WO | 2013011156 | A2 | | 1/2013 |
| WO | 2013045301 | A1 | | 4/2013 |
| WO | 2014180945 | A1 | | 11/2014 |
| WO | 2014180952 | A1 | | 11/2014 |

OTHER PUBLICATIONS

International Search Report and Written Opinion of the International Searching Authority for corresponding application PCT/EP2015/073374 dated Jan. 12, 2016.

G. Skouroumis, et al., "Synthesis of 1,3,4,5-Tetrahydro-2-Benzoxepin Derivatives as Conformationally Restricted Analogues of Cyclmenaldehyde-Type Compounds and as Intermediates for Highly Odour-Active Homologues", Helvetica Chimica Acta, Verlag Helvetica Chimica Acta, CH, vol. 79, No. 4, Jan. 1, 1996, pp. 1095-1109.

H. Chen, et al., "Facile Synthesis of (E)-Alkenyl Aldehydes from Allyl Arens or Alkenes via Pd(II)-Catalyzed Direct Oxygenation of Allyci C—H Bond", American Chemical Society, Organic Letters, vol. 13, No. 5, pp. 992-994, 2011 (XP-002752191).

C.G. Hunter, et al., "Studies on the Oral Toxicity of p-tert—butyl Benzoic Acid in Rats", Fd Cosmet. Toxicol., vol. 3, pp. 289-298, Pergamon , Great Britain,1965.

S. A. McCune, et al., "Inhibition of Hepatic Gluconeogenesis of Lipogenesis by Benzoic Acid, p-tert—butyl Butylbenzoic Acid, and a Structurally Related Hypolipidemic Agent SC-33459", Archives of Biochemistry and Biophysics, vol. 214, No. 1, pp. 124-133,1982.

G. Skouroumounis, et al., "96 Synthesis of 1,3,4,5-Tetrahydro-2-benzoxepin Derivatives as Conformationally Restricted Analogues of Cyclamenaldehyde-Type Compounds and as Intermediates of Highly Odour-Active Homologues", vol. 79, pp. 1095-1109, 1996 (XP-002752190).

* cited by examiner

PHENYL BASED COMPOUNDS SUBSTITUTED WITH ALDEHYDE MOIETIES AND THEIR USE IN PERFUMERY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This is an application filed under 35 USC 371 of PCT/EP2015/073374 filed 9 Oct. 2015, which in turn claims the benefit of PCT/CN2014/090675 filed 10 Nov. 2014. The present application claims all available priority benefits to the foregoing applications, and also herein incorporates by reference the entirety of their disclosures as if set forth herein.

This invention relates to perfume ingredients and perfume preparations containing same. In particular, the invention relates to said perfume ingredients or perfume preparations that exhibit green odour characteristics, being important aspects of muguet (lily of the valley) odour characteristics. Still more particularly, the invention relates to said perfume preparations that contain no, or substantially no, Lilial™. The invention further relates to methods of making said perfume ingredients and perfume preparations, as well as the use of said perfume ingredients and perfume preparations in fine fragrances and consumer products, such as personal care and household care products. The invention also relates to said fine fragrances and consumer products containing said perfume ingredients or perfume preparations.

Compounds having muguet odour characteristics are very sought after perfume ingredients. These compounds are important ingredients in floral bases and can act as harmonizers across many different types of fragrance creations. Compounds of this type are used widely in consumer products, such as personal care and consumer care products, as well as in fine perfumery, to generate pleasant odours or to mask unpleasant odours. One of the important aspects of muguet odour characteristics is the green odour, in particular the green aldehydic or green floral odour.

An excellent perfume ingredient widely valued for its muguet odour note is Lilial™ Lilial™ is an example of an aryl-substituted alkanal, more particularly an aryl-substituted propanal. Specifically, its chemical name is 3-(4-tert-butylphenyl)-2-methylpropanal (CAS 80-54-6). This compound has found wide use in fine perfumery as well as in personal and household care products. However, its use has come under regulatory scrutiny in view of recent findings that it exhibits toxic effects on the reproductive organs of male rats and dogs. No effects were found in studies with mice, guinea-pigs and primates, nevertheless, under the Global Harmonized System (GHS) classification system this compound is classified as a CMR2 material. For CMR category 2 materials, it is necessary to establish that quantities proposed for use are harmless to consumers. In view of the regulatory situation of Lilial™ there is a need to replace it with other perfume ingredients.

WO2010105 873 addresses the problem of replacing Lilial™. The proposed solution resides in the use of mixtures of known ingredients commonly found in the perfumery palette in order to recreate odour characteristics substantially similar to those of Lilial™.

Likewise, WO2009027957 proposes a solution residing in the formulation of combinations of known perfume ingredients from the perfumery palette.

WO2013045301 also propose a solution to Lilial™ replacement, which resides in the selection of mixtures of ingredients including the compound Lilyflore™ and a certain indanyl propanal compound, in combination with other secondary perfuming ingredients.

The applicant has now found compounds that can be employed as perfume ingredients in perfume compositions and consumer products. More particularly, the applicant has found compounds that possess desirable green odour characteristics, in particular green aldehydic or green floral odour characteristics. Still more particularly, the applicant has found compounds that possess odour characteristics, which may be perceived and recognised by perfumers as being related to the odour of Lilial™ and so can serve in replacements for Lilial™. Furthermore, the compounds may have similar or even improved perfume performance compared with Lilial™. Finally, the applicant has found compounds that do not attract the regulatory concerns associated with Lilial™. In particular, the applicant has found that aryl-substituted alkanal perfume ingredients that are structurally related to Lilial™ but which contain a substituent on the aryl ring, which is positioned ortho or meta to the group bearing the aldehyde functionality, have interesting odour characteristics, but surprisingly carry with them none or significantly less of the CMR-related issues associated with Lilial™ as indicated by in vitro data.

In a first aspect of the present invention there is provided a compound represented by the formula 1

Formula 1

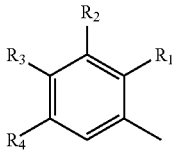

wherein $R_1$ is H, or when $R_2$ and $R_3$ is H, then $R_1$ is $CHR_5CHR_6CHO$, $CR_5{=}CR_6CHO$ or $C(CH_3)CHO$, wherein $R_5$, $R_6$ each independently may represent H or methyl;

$R_2$ is H, or when $R_1$ and $R_3$ is H, then $R_2$ is $CHR_5CHR_6CHO$, $CR_5{=}CR_6CHO$ or $C(CH_3)CHO$, wherein $R_5$, $R_6$ each independently may represent H or methyl;

$R_3$ is H, or when $R_1$ and $R_2$ is H, then $R_3$ is $CHR_5CHR_6CHO$, $CR_5{=}CR_6CHO$ or $C(CH_3)CHO$, wherein $R_5$, $R_6$ each independently may represent H or methyl; and $R_4$ is methyl or a branched or linear, saturated or unsaturated, unsubstituted or substituted (optionally with cyclopropyl groups), $C_2$-$C_7$ alkyl or alkenyl residue, preferentially isobutyl, isoamyl.

The compounds of the present invention possess specific odour and good performance characteristics, and the compounds may be used for the reconstitution for the odour of Lilial™ and so can serve in replacements for Lilial™.

Furthermore, compounds of the present invention can generate particularly substantive and long-lasting odour characteristics, and they can contribute to particularly substantive and long-lasting muguet odour characteristics.

It is particularly preferred to provide a compound represented by the formula 1

Formula 1

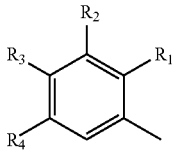

wherein $R_1$ is H, or when $R_2$ and $R_3$ is H, then $R_1$ is $C(CH_3)CHO$;

$R_2$ is H, or when $R_1$ and $R_3$ is H, then $R_2$ is $CHR_5CHR_6CHO$, $CR_5{=}CR_6CHO$ or $C(CH_3)CHO$, wherein $R_5$, $R_6$ each independently may represent H or methyl;

$R_3$ is H, or when $R_1$ and $R_2$ is H, then $R_3$ is $CHR_5CHR_6CHO$, $CR_5{=}CR_6CHO$ or $C(CH_3)CHO$, wherein $R_5$, $R_6$ each independently may represent H or methyl; and $R_4$ is methyl or a branched or linear, saturated or unsaturated, unsubstituted or substituted (optionally with cyclopropyl groups), $C_2$-$C_7$ alkyl or alkenyl residue, preferentially isobutyl, isoamyl.

In another aspect of the invention, there is provided a compound of formula 2

Formula 2

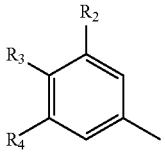

wherein $R_2$ is H, or when $R_3$ is H, then $R_2$ is $CHR_5CHR_6CHO$, $CR_5{=}CR_6CHO$ or $C(CH_3)CHO$, wherein $R_5$, $R_6$ each independently may represent H or methyl;

$R_3$ is H, or when $R_2$ is H, then $R_3$ is $CHR_5CHR_6CHO$, $CR_5{=}CR_6CHO$ or $C(CH_3)CHO$, wherein $R_5$, $R_6$ each independently may represent H or methyl; and $R_4$ is methyl or a branched or linear, saturated or unsaturated, unsubstituted or substituted (optionally with cyclopropyl groups), $C_2$-$C_7$ alkyl or alkenyl residue, preferentially isobutyl, isoamyl.

The compounds represented by formula 2 possess specific odour and good performance characteristics, and the compounds may be used for the reconstitution for the odour of Lilial™ and so can serve in replacements for Lilial™.

Furthermore, compounds of the present invention can generate particularly substantive and long-lasting green odour characteristics, and they can contribute to particularly substantive and long-lasting muguet odour characteristics.

In a further aspect of the invention, there is provided a compound represented by formula 3

Formula 3

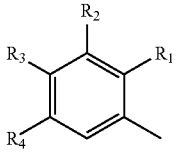

wherein $R_1$ is H, or when $R_2$ and $R_3$ is H, then $R_1$ is $C(CH_3)CHO$;
$R_2$ is H, or when $R_1$ and $R_3$ is H, then $R_2$ is $C(CH_3)CHO$;
$R_3$ is H, or when $R_1$ and $R_2$ is H, then $R_3$ is $C(CH_3)CHO$; and $R_4$ is methyl or a branched or linear, saturated or unsaturated, unsubstituted or substituted (optionally with cyclopropyl groups), $C_2$-$C_7$ alkyl or alkenyl residue, preferentially isobutyl, isoamyl.

Some of the compounds of the present invention, represented by one of the formulae 1, 2 or 3, are particularly impactful perfume ingredients. The impact that a perfume ingredient exerts is related to its Odour Value. Odour Value is the ratio of vapour pressure to detection threshold concentration.

Some of the compounds have relatively high Odour Values. For example, the structure related compound

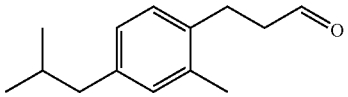

having a substituent on the aryl ring, which is positioned ortho to the group bearing the aldehyde functionality, has an Odour Value of 559'071. Related perfume ingredients are not impactful by comparison. For example Lilial™ has an odour value of only 32'978 whereas cyclamen aldehyde has an Odour Value of only 21'986.

The relatively high Odour Value of several compounds of the present invention is significant in that there is a need for sustainability and the provision of impactful perfume ingredients enables perfumers to create desirable fragrance accords with lower concentrations of materials.

However, also compounds of the present invention with a lower Odour Value might be of interest due to their specific odour.

In a further aspect of the invention, it was surprisingly found that some compounds represented by formula 2 may modify the odour of 3-(4-isobutyl-2-methylphenyl)propanal. Therefore, it is preferred to provide mixtures of 3-(4-isobutyl-2-methylphenyl)propanal with not more than 20% by weight, preferably not more than 15% by weight, and even more preferentially 10% by weight of the total amount of compounds represented by formula 2. Preferably, the amount of compounds represented by formula 2 in mixtures with 3-(4-isobutyl-2-methylphenyl)propanal is not more than 5% by weight and even more preferentially not more than 3.5% by weight. Particularly preferred, the total amount of compounds represented by formula 2 is not more than 1.5% by weight.

In a specific aspect of the invention, it is preferred to use a mixture of 3-(4-isobutyl-2-methylphenyl)propanal and 3-(2-isobutyl-4-methyl phenyl)propanal in a ratio of 80:20 by weight, particularly preferred 85:15 by weight, more preferred 90:10 by weight, even more preferred 95:5 by weight.

Furthermore, in a specific aspect of the invention, it is preferred to use 3-(4-isobutyl-2-methylphenyl)propanal in mixtures with not more than 3.5%, or even not more than 1.5% by weight of 3-(2-isobutyl-4-methylphenyl)propanal.

However, when used alone or in admixtures with other fragrance ingredients, the effective amounts of the compounds represented by formula 2, in particular 3-(2-isobutyl-4-methylphenyl)propanal, might be significantly higher.

The regulatory issues surrounding Lilial™ are born from the fact that it is enzymatically degraded in rats and dogs to tert-butyl benzoic acid (t-BBA), which is known to inhibit glucose synthesis and fatty acid synthesis in vitro (McCune et al, Arch Biochem Biophys (1982) 214 (1): 124-133).

tert-Butyl benzoic acid is known to cause testicular effects in male rats (Hunter et al. Food Cosmet. Toxicol. 1965, 3: 289-298; Cagen et al. J. Am. Coll. Toxicol. 1989, 8 (5): 1027-1038).

In contrast, the compounds of the present invention are not or at least less susceptible to enzyme-mediated degradation to corresponding benzoic acid derivatives in vitro. This was indeed a very surprising result considering their close structural similarity to Lilial™.

The applicant's surprising discovery that aryl-substituted alkanal perfume ingredients substituted on the ring at a position ortho or meta to the group bearing the aldehyde functionality are not or in a lower amount converted to their corresponding benzoic acid derivatives, provides an insight not heretofore appreciated in the art, which enables perfumers to employ a class of compounds that although being structurally related to Lilial™ (and therefore possessing remarkably olfactive properties), nevertheless do not raise regulatory issues.

In order to study in vitro metabolism in rat hepatocytes, Lilial™ and compounds of the present invention may be incubated in the presence of rat hepatocytes in suspension. Reduction in the concentration of Lilial™and the compounds of the present invention and formation of any of the corresponding benzoic acid derivatives may be analysed by GC-MS.

In another aspect of the present invention there is provided a compound as herein above defined, which after incubation with hepatocytes isolated from rats, is substantially free of its corresponding benzoic acid degradation product. By "substantially free" is meant that if it is present it is below levels of detection, e.g. less than 1%, more particularly less than 1% to 0%. As such, compounds of the present invention are very interesting fragrance ingredients.

Accordingly, the invention provides in another of its aspects the use of a compound defined hereinabove as a perfume ingredient.

The invention provides in another of its aspects the use of a compound defined hereinabove in a perfume composition, alone or in admixtures, as a replacement for aryl-substituted alkanal odourants, more particularly aryl-substituted propanal odourants, which are unsubstituted on the aryl ring at a position ortho or meta to the substituent bearing the aldehyde functionality, in particular Lilial™.

In another aspect of the invention there is provided a method of imparting a green odour characteristic to a perfume composition, said method comprising the step of incorporating a compound defined hereinabove into said perfume composition.

In yet another aspect of the invention there is provided a perfume composition comprising a compound defined hereinabove.

In yet another aspect of the invention there is provided a perfume composition possessing green aspects of muguet odour characteristics, comprising a compound defined hereinabove.

In yet another aspect of the present invention there is provided a perfume composition comprising a compound defined hereinabove that has a reduced amount of or is free of any aryl-substituted propanal odourants, which are unsubstituted on the aryl ring at a position ortho or meta to the substituent bearing the aldehyde functionality, in particular Lilial™.

A perfume composition according to the present invention can be made up entirely by one or more of the compounds of the present invention. However, a perfume composition may also contain, in addition to one or more of the compounds of present invention, one or more additional perfume ingredients.

Compounds of the present invention may be present in a perfume composition in any amount depending on the particular olfactive effect that a perfumer wishes to achieve. In a particular embodiment of the present invention, a perfume composition of the present invention may contain compounds defined hereinabove in an amount of 0.1 to 100% by weight of said composition.

If one or more additional perfume ingredients are employed, they may be selected from perfume ingredients known in the art.

Preferably, the at least one additional perfume ingredient that may be employed in a perfume composition possesses muguet odour characteristics, like 3-(4-isobutyl-2-methylphenyl)propanal.

In particular, said perfume ingredients that may be employed in a perfume composition according to the invention include (E/Z)-9-hydroxy-5,9-dimethyldec-4-enal, 6-methoxy-2,6-dimethylheptan-1-al (methoxymelonal), 5,9-dimethyl-4,8-decadienal (geraldehyde), beta-methyl-3-(1-methylethyl)benzenepropanal (Florhydral), octahydro-8,8-di methylnaphthalene-2-carbaldehyde (Cyclomyral), alpha-methyl-1,3-benzodioxole-5-propionaldehyde (helional), 5-methyl-2-(1-methylbutyl)-5-propyl-1,3-dioxan (Troenan), 3-(o-ethyl phenyl)-2,2-dimethylpropionaldehyde (Floralozone), farnesol, 3,7,11-trimethyldodeca-1,6,10-trien-3-ol, optionally as an isomeric mixture (nerolidol), 2-methyl-4-phenylbutan-2-ol (di methylphenylethylcarbinol), cis-4-(isopropyl)cyclohexanemethanol (Mayol), 1-(1-hydroxyethyl)-4-(1-methylethyl)cyclohexane (optionally as a mixture of the diastereoisomers) (mugetanol), (4-methyl-3-pentenyl)cyclohexenecarbaldehyde (Citrusal), cyclohexyl salicylate, hexyl salicylate, benzyl salicylate, amyl salicylate, 3-(p-(2-methylpropyl)phenyl)-2-methylpropionaldehyde (Silvial), 3-p-cumenyl-2-methylpropionaldehyde (cyclamenaldehyde), mixtures of: cis-tetrahydro-2-isobutyl-4-methylpyran-4-ol; trans-tetrahydro-2-isobutyl-4-methylpyran-4-ol; (Florol), triethyl citrate and dipropylene glycol.

Said perfume ingredients may additionally include Amyl Salicylate (2050-08-0); Aurantiol® (89-43-0); Benzyl Salicylate (118-58-1); Cis-3-hexenyl Salicylate (65405-77-8); Citronellyl Oxyacetaldehyde (7492-67-3); Cyclemax (7775-00-0); Cyclohexyl Salicylate (25485-88-5); Cyclomyral® (68738-94-3); Citronellol (106-22-9); Geraniol (106-24-1); Cyclopentol Hc 937165 (84560-00-9); Cymal (103-95-7); Dupical (30168-23-1); Ethyl Linalool (10339-55-6); Floral Super (71077-31-1); Florhydral® (125109-85-5); Florol® (63500-71-0); Gyrane (24237-00-1); Hexyl Salicylate (6259-76-3); Helional™ (1205-17-0); Hydroxycitronellal (107-75-5); Linalool (78-70-6); Lyral® (31906-

04-4); Majantol® (103694-68-4); Mayol® (13828-37-0); Melafleur (68991-97-9); Melonal (106-72-9); Mugetanol (63767-86-2); Muguesia (56836-93-2); Muguet alcohol (13351-61-6); Verdantiol (91-51-0); Peonile® (10461-98-0); Phenoxanol® (55066-48-3); Rossitol® (215231-33-7); Silvial® (6658-48-6); Suzural (6658-48-6); Muguol® (18479-57-7); Tetrahydro Linalol (78-69-3); Acalea (84697-09-6); Dihydro Iso Jasmonate (37172-53-5); Hexyl Cinnamic Aldehyde (101-86-0); Hedione® (24851-98-7); Acetoin (513-86-0); Adoxal (141-13-9); Aldolone® (207228-93-1); Ambrocenide® (211299-54-6); Ambroxan (3738-00-9); Azurone® (362467-67-2); Bacdanol® (28219-61-6); Calone 1951® (28940-11-6); Cetalox® (3738-00-9); Cinnamic alcohol (104-54-1); Citral (5392-40-5); Cyclabute (67634-20-2); Cyclacet® (5413-60-5); Cyclaprop® (17511-60-3); Cyclohexadecanolide (109-29-5); Cyclohexadecenone (3100-36-5); Cyclopentadecanone (507-72-7); Delta Da mascone (57378-68-4); Ebanol® (67801-20-1); Elintaal Forte (40910-49-4); Ethyl Vanillin (121-32-4); Ethylene Brassylate (105-95-3); Exaltenone 942008 (14595-54-1); Exaltolide Total 935985 (106-02-5); Floralozone (67634-14-4); Fructalate (72903-27-6); Gamma Decalactone (706-14-9); Habanolide (111879-80-2); Helvetolide® (141773-73-1); Hexamethylindanopyran (1222-05-5); Hydroxyambran® (118562-73-5); Iso E Super® (54464-57-2); Iso Hexenyl Cyclohexenyl Carboxaldehyde (37677-14-8); Jasmal (18871-14-2); Javanol® (198404-98-7); Lauric Aldehyde (112-54-9); Mefranal (55066-49-4); Muscenone (63314-79-4); Tonalid® (1506-02-1); Nectaryl® (95962-14-4); Norlim Banol (70788-30-6); Para Hydroxy Phenyl Butanone (5471-51-2); Pino Acetaldehyde (33885-51-7); Romandolide® (236391-76-7); Sanjinol (28219-61-6); Silvanone® Supra (109-29-5/507-72-7); Terpineol (8000-41-7); Vanillin (121-33-5); and Velvione® (37609-25-9), wherein, the figures in parentheses are CAS numbers.

A perfume composition need not be limited to the perfume ingredients listed above. Other perfume ingredients commonly used in perfumery may be employed, for example any of those ingredients described in "Perfume and Flavour Chemicals", S. Arctander, Allured Publishing Corporation, 1994, IL, USA, which is incorporated herein by reference, including essential oils, plant extracts, absolutes, resinoids, odourants obtained from natural products and the like.

The perfume ingredients contained in said perfume composition are described above, but of course, the perfume composition may not be limited to the stated ingredients. In particular, perfume mixtures may comprise adjuvants that are commonly employed in perfume formulations. The term "adjuvants" refers to an ingredient that might be employed in a perfume composition for reasons other than, or not specifically, related to the composition's olfactive performance. For example, an adjuvant may be an ingredient that acts as an aid to processing a perfume ingredient or ingredients, or a composition containing said ingredient(s), or it may improve handling or storage of a perfume ingredient or composition containing same. It might also be an ingredient that provides additional benefits such as imparting colour or texture. It might also be an ingredient that imparts light resistance or chemical stability to one or more ingredients contained in a perfume ingredient or composition containing same. A detailed description of the nature and type of adjuvants commonly used in perfume mixture or compositions containing same cannot be exhaustive, but it has to be mentioned that said ingredients are well known to a person skilled in the art. Examples of adjuvants include solvents and co-solvents; surfactants and emulsifiers; viscosity and rheology modifiers; thickening and gelling agents; preservative materials; pigments, dyestuffs and colouring matters; extenders, fillers and reinforcing agents; stabilisers against the detrimental effects of heat and light, bulking agents, acidulants, buffering agents and antioxidants.

Furthermore, any one or more of the perfume ingredients or adjuvants employed in the present invention might be formulated in a delivery vehicle if desired to provide a desired effect. Delivery vehicles may include encapsulates. Alternatively, a delivery vehicle may be in the form of a solid support, e.g. a polymeric support material onto which one or more perfume ingredients or adjuvants may be chemically or physically bound. Still further, one or more perfume ingredients or adjuvants may be dissolved or dispersed in a matrix material, which serves to control the rate at which said ingredient or ingredients emanates therefrom. In yet an alternative embodiment, one or more ingredients or adjuvants may be supported on a porous substrate, such as a cyclodextrin or a zeolite or other inorganic material. In a still further embodiment, one or more perfume ingredients may be provided in the form of a pro-perfume, which will react in a suitable environment to release the perfume ingredient in a controlled manner.

Preferably, in case of further perfume ingredients bearing a carbonyl functionality, the corresponding pro-perfume is a reaction product of a primary and/or secondary amine compound and the perfume ingredient.

In particular it is preferred that such a pro-perfume, also known as fragrance precursor, is a reaction product of a suitable amino compound and a compound represented by the formula 1

Formula 1

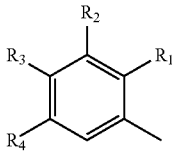

wherein $R_1$ is H, or when $R_2$ and $R_3$ is H, then $R_1$ is $CHR_5CHR_6CHO$, $CR_5{=}CR_6CHO$ or $C(CH_3)CHO$, wherein $R_5$, $R_6$ each independently may represent H or methyl;

$R_2$ is H, or when $R_1$ and $R_3$ is H, then $R_2$ is $CHR_5CHR_6CHO$, $CR_5{=}CR_6CHO$ or $C(CH_3)CHO$, wherein $R_5$, $R_6$ each independently may represent H or methyl;

$R_3$ is H, or when $R_1$ and $R_2$ is H, then $R_3$ is $CHR_5CHR_6CHO$, $CR_5{=}CR_6CHO$ or $C(CH_3)CHO$, wherein $R_5$, $R_6$ each independently may represent H or methyl; and $R_4$ is methyl or a branched or linear, saturated or unsaturated, unsubstituted or substituted (optionally with cyclopropyl groups), $C_2$-$C_7$ alkyl or alkenyl residue, preferentially isobutyl, isoamyl.

By such a reaction, different products may be obtained, for example the corresponding imine, enamine, hemi-aminal or aminal.

A suitable amino compound for formation of the above mentioned pro-perfume can be selected from the group consisting of aromatic amines, in particular methyl 2-aminobenzoate (methyl anthranilate), 2-amino-acetophenone, ortho, meta or para aminobenzoates; primary or secondary aliphatic amines, preferably C8-C30 linear or branched alkylamines or alkyldiamines; etheramines; ethylene- and propylene-amines; amino acids and derivatives; polyamines, in particular primary and secondary polyetheramines, polyethyleneimines, polypropyleneimines, polyamidoamines, polyaminoacids, polyvinylamines, polyethylene glycol) bis(a mine), amino substituted polyvinylalcohols; N-(3-aminopropyl)imidazole, nipecotamide, skatole and indole.

The pro-perfume is suitable to release the compound represented by the formula 1 as defined above.

In a preferred embodiment such a pro-perfume, also known as fragrance precursor, is a reaction product of a suitable amino compound and a compound represented by the formula 2

Formula 2

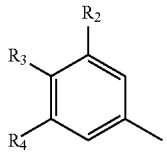

wherein $R_2$ is H, or when $R_3$ is H, then $R_2$ is $CHR_5CHR_6CHO$, $CR_5{=}CR_6CHO$ or $C(CH_3)CHO$, wherein $R_5$, $R_6$ each independently may represent H or methyl;

$R_3$ is H, or when $R_2$ is H, then $R_3$ is $CHR_5CHR_6CHO$, $CR_5{=}CR_6CHO$ or $C(CH_3)CHO$, wherein $R_5$, $R_6$ each independently may represent H or methyl; and $R_4$ is methyl or a branched or linear, saturated or unsaturated, unsubstituted or substituted (optionally with cyclopropyl groups), $C_2$-$C_7$ alkyl or alkenyl residue, preferentially isobutyl, isoamyl.

In another preferred embodiment such a pro-perfume is a reaction product of a suitable amino compound and a compound represented by the formula 3

Formula 3

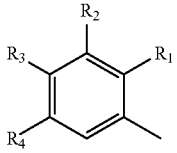

wherein $R_1$ is H, or when $R_2$ and $R_3$ is H, then $R_1$ is $C(CH_3)CHO$;

$R_2$ is H, or when $R_1$ and $R_3$ is H, then $R_2$ is $C(CH_3)CHO$;

$R_3$ is H, or when $R_1$ and $R_2$ is H, then $R_3$ is $C(CH_3)CHO$; and $R_4$ is methyl or a branched or linear, saturated or unsaturated, unsubstituted or substituted (optionally with cyclopropyl groups), $C_2$-$C_7$ alkyl or alkenyl residue, preferentially isobutyl, isoamyl Alternatively, the pro-perfume suitable to release a compound of formula 1, in particular a compound of formula 2 or 3, may be provided as a product of a Knoevenagel condensation or an aldol condensation reaction, as an oxidative cleavable pro-perfume (e.g. as a 2-alkyl-1-(4-(4-methoxyphenyl)but-3-en-1-yl)-4-methylbenzene derivative or a 3-alkyl-1-(4-(4-methoxyphenyl)but-3-en-1-yl)-5-methylbenzene derivative) or an acetal or hemi-acetal.

Having regard to the foregoing, it will be appreciated that a perfume composition may be at least partly in solid form, in gel form, in foam form and/or liquid form. If it is present in solid form, it then may take the form of granules, powders or tablets.

The present invention provides in another of its aspects a fine fragrance or consumer product, such as a personal care or household care composition that is perfumed by a compound represented by the formula 1

Formula 1

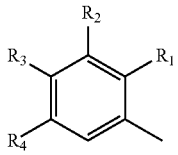

$R_1$ is H, or when $R_2$ and $R_3$ is H, then $R_1$ is $CHR_5CHR_6CHO$, $CR_5{=}CR_6CHO$ or $C(CH_3)CHO$, wherein $R_5$, $R_6$ each independently may represent H or methyl;

$R_2$ is H, or when $R_2$ and $R_3$ is H, then $R_2$ is $CHR_5CHR_6CHO$, $CR_5{=}CR_6CHO$ or $C(CH_3)CHO$, wherein $R_5$, $R_6$ each independently may represent H or methyl;

$R_3$ is H, or when $R_1$ and $R_2$ is H, then $R_3$ is $CHR_5CHR_6CHO$, $CR_5{=}CR_6CHO$ or $C(CH_3)CHO$, wherein $R_5$, $R_6$ each independently may represent H or methyl; and $R_4$ is methyl or a branched or linear, saturated or unsaturated, unsubstituted or substituted (optionally with cyclopropyl groups), $C_2$-$C_7$ alkyl or alkenyl residue, preferentially isobutyl, isoamyl.

In a particular embodiment the invention provides a fine fragrance or consumer product, such as a personal care or household care composition that is perfumed by a compound represented by the formula 2

Formula 2

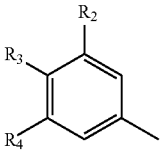

wherein $R_2$ is H, or when $R_3$ is H, then $R_2$ is $CHR_5CHR_6CHO$, $CR_5{=}CR_6CHO$ or $C(CH_3)CHO$, wherein $R_5$, $R_6$ each independently may represent H or methyl;

$R_3$ is H, or when $R_2$ is H, then $R_3$ is $CHR_5CHR_6CHO$, $CR_5{=}CR_6CHO$ or $C(CH_3)CHO$, wherein $R_5$, $R_6$ each independently may represent H or methyl; and $R_4$ is methyl or a branched or linear, saturated or unsaturated, unsubstituted or substituted (optionally with cyclopropyl groups), $C_2$-$C_7$ alkyl or alkenyl residue, preferentially isobutyl, isoamyl.

In another particular embodiment the invention provides a fine fragrance or consumer product, such as a personal care or household care composition that is perfumed by a compound represented by the formula 3

Formula 3

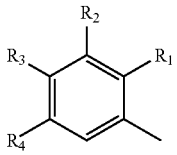

wherein $R_1$ is H, or when $R_2$ and $R_3$ is H, then $R_1$ is $C(CH_3)CHO$;

$R_2$ is H, or when $R_1$ and $R_3$ is H, then $R_2$ is $C(CH_3)CHO$;

$R_3$ is H, or when $R_1$ and $R_2$ is H, then $R_3$ is $C(CH_3)CHO$; and $R_4$ is methyl or a branched or linear, saturated or unsaturated, unsubstituted or substituted (optionally with cyclopropyl groups), $C_2$-$C_7$ alkyl or alkenyl residue, preferentially isobutyl, isoamyl.

In yet more particular embodiments of the present invention there is provided a fine fragrance or consumer product, such as a personal care or household care composition that is perfumed by one or more compounds selected from 3-(3-isobutyl-5-methylphenyl)propanal, 3-(2-isobutyl-4-methyl phenyl)propanal, (E)-3-(2-isobutyl-4-methyl phenyl)acrylaldehyde and 2-(2-isobutyl-4-methyl phenyl)-propanal.

The compounds defined above, when added to a fine fragrance or consumer product, such as a personal care or household care composition, impart a characteristic odour to said compositions, preferably a green odour. According to another aspect of the present invention there is provided a method of imparting specific odour characteristics, preferably green odour characteristics, to a fine fragrance or consumer product, such as a personal care or household care composition comprising the step of adding to said composition a compound defined above or a perfume composition containing said compound.

In yet another aspect of the invention there is provided a method of imparting specific odour characteristics, in particular green odour characteristics, to a fine fragrance or consumer product, such as a personal care or household care composition, comprising the step of selectively adding to said fine fragrance or consumer product an aryl-substituted alkanal compound defined above, and selectively excluding from said fine fragrance or consumer product any aryl-substituted alkanal compounds, which are unsubstituted on the ring at the position ortho or meta to the substituent containing aldehyde functionality.

In yet another aspect of the invention there is provided a method of imparting green odour characteristics to a fine fragrance or consumer product, such as a personal care or household care composition, comprising the step of adding thereto an aryl-substituted alkanal compound defined above, and selectively excluding from said fine fragrance or consumer product any aryl-substituted alkanal compounds, which are unsubstituted on the ring at the position ortho or meta to the substituent containing aldehyde functionality, said selective addition or exclusion being based on the susceptibility of said compounds to enzymatically-mediated degradation to their benzoic acid derivatives when incubated with hepatocytes isolated from rats, said compounds being suitable for addition on the basis that they do not degrade to their benzoic acid derivatives under test conditions, whereas said compounds being excluded on the basis that they do degrade to their benzoic acid derivatives under test conditions.

In yet another aspect of the invention there is provided a perfume composition comprising an aryl-substituted alkanal compound bearing a substituent on the aryl ring ortho or meta to a substituent bearing the aldehyde functionality, in a suitable container, together with labelling that does not contain any CMR2 classification.

Consumer products, such as personal and household care compositions include, but are not limited to a textile treatment product, an ironing aid, a cleaning cloth, a laundry detergent, a cleaning product, in particular, for hard and/or soft surfaces, a household cleaner, a care product, a wash care product, a laundry care product, a room fragrancer, and air freshener, a conditioner, a colorant, a fabric conditioner, a conditioning substrate, a pharmaceutical, a crop protection product, a polish, a food, a cosmetic product, a fertilizer, a building material, an adhesive, a bleach, a decalcifier, an autocare product, floorcare product, cookercare product, leathercare product or furniture care product, a scourer, a disinfectant, a fragrancer, a mold remover and/or a precursor of the aforementioned products.

The skilled person is fully aware of the applicability of perfume ingredients, and compositions to fine fragrance applications, as well as all manner of consumer product applications, such as personal and house hold care compositions and a very detailed description of such compositions is not warranted here. However, specific compositions that can be mentioned include cleaning compositions; autocare compositions; Cosmetic compositions; textile treatment compositions and air freshener and air care compositions.

Cleaning products include:

Toilet cleaners or lavatory cleaners, in other words, products for cleaning lavatory bowls and urinals, these products being supplied preferably in the form of powders, blocks, tablets or liquids, preferably gels. Besides other typical ingredients such as surfactants, they generally include organic acids e.g., citric acid and/or lactic acid) or sodium hydrogen sulfate, amidosulfuric acid or phosphoric acid for removing limescale or urine scale;

Pipe-cleaning products or drain cleaners. These are typically strongly alkaline products which serve in general to remove pipe blockages comprising organic materials-such as hair, fat, food residues, soap deposits, and the like. Additions of Al powder or Zn powder may serve for the formation of H2 gas with an effervescence effect. Possible ingredients are commonly alkalis, alkaline salts, oxidizing agents, and neutral salts. Supply forms in powder form preferably also include sodium nitrate and sodium chloride. Pipe-cleaning products in liquid form may preferably also include hypochlorite. There are also enzyme-based drain cleaners as well. Acidic products are likewise possible;

Universal or all-purpose or general-purpose cleaners. These are cleaners which can be used universally for all hard surfaces in the household and in commerce that can be wiped down wet or damp. Generally speaking, they are neutral or slightly alkaline or slightly acidic products, especially liquid products. All-purpose or general-purpose cleaners generally contain surfactants, builders, solvents and hydrotropes, dyes, preservatives, and the like;

All-purpose cleaners with special disinfectant properties. They additionally include active antimicrobial ingredients (e.g., aldehydes, alcohols, quaternary ammonium compounds, amphoteric surfactants, triclosan);

Sanitary cleaners. These are products for cleaning in bath and toilet. The alkaline sanitary cleaners are used preferably for removing fatty soiling, whereas the acidic sanitary cleaners are employed in particular, for removing limescale. Sanitary cleaners advantageously also have a considerable disinfectant action, particularly the strongly alkaline sanitary cleaners that contain chlorine;

Oven cleaners or grill cleaners which may be supplied in the form of gels or foam sprays. They generally serve for removing burnt-on or carbonized food residues. Oven cleaners are preferably given a strongly alkaline formulation using, for example, sodium hydroxide, sodium metasilicate, 2-aminoethanol. In addition they generally contain anionic and/or nonionic surfactants, water-soluble solvents, and, in some cases, thickeners such as polycarboxylates and carboxymethylcellulose;

Metal polishes. These are cleaners for particular types of metal such as stainless steel or silver. Stainless steel cleaners preferably contain, besides acids (preferably up to 3% by weight, e.g., citric acid, lactic acid), surfactants (in particular, up to 5% by weight, preferably nonionic and/or anionic surfactants), and water, solvents as well (preferably up to 15% by weight) to remove fatty soiling, and also further compounds such as thickeners and preservatives. Very fine polishing structures are included, furthermore, in products for preferably bright stainless steel surfaces. Silver polishes, in turn, may be provided in an acidic formulation. In particular, for removing black deposits of silver sulfide they contain, preferably, complexing agents (e.g., thiourea, sodium thiosulfate). Typical supply forms are polishing cloths, dipping baths, pastes, and liquids. Dark discolorations (oxide layers) are removed using copper cleaners and nonferrous-metal cleaners (e.g., for brass and bronze). They generally have a weakly alkaline formulation (preferably with ammonia) and in general contain polishing agents and also, preferably, ammonium soaps and/or complexing agents;

Glass cleaners and window cleaners. These products serve preferably to remove dirt, especially greasy dirt, from glass surfaces. Preferably they contain compounds such as anionic and/or nonionic surfactants (in particular, up to 5% by weight), ammonia and/or ethanolamine (in particular, up to 1% by weight), ethanol and/or 2-propanol, glycol ethers (in particular, 10-30% by weight), water, preservatives, dyes, anti-misting agents and the like; and Special-purpose cleaning products, examples being those for glass-ceramic hobs, and also carpet cleaners and stain removers.

Autocare products include:

Paint preservers, paint polishes, paint cleaners, wash preservers, shampoos for auto washing, auto-wash and wax products, polishes for trim metals, protective films for trim metals, plastics cleaners, tar removers, screen cleaners, engine cleaners, and the like.

Cosmetic products include:

(a) cosmetic skincare products, especially bath products, skin washing and cleansing products, skincare products, eye makeup, lip care products, nail care products, intimate care products, foot care products;

(b) cosmetic products with specific effects, especially sunscreens, tanning products, de-pigmenting products, deodorants, antiperspirants, hair removers, shaving products, perfumes;

(c) cosmetic dental-care products, especially dental and oral care products, tooth care products, cleaners for dental prostheses, adhesives for dental prostheses; and (d) cosmetic hair care products, especially hair shampoos, hair care products, hair setting products, hair-shaping products, and hair coloring products.

Textile treatment products include:

Detergents or fabric conditioners, for example, in either liquid or solid form.

Air fresheners and room fragrancers include:

Products that contain preferably volatile and usually pleasant-smelling compounds which advantageously can even in very small amounts mask unpleasant odours. Air fresheners for living areas contain, in particular, natural and synthetic essential oils such as pine needle oils, citrus oil, eucalyptus oil, lavender oil, and the like., in amounts for example of up to 50% by weight. As aerosols they tend to contain smaller amounts of such essential oils, by way of example less than 5% or less than 2% by weight, but additionally include compounds such as acetaldehyde (in particular, <0.5% by weight), isopropyl alcohol (in particular, <5% by weight), mineral oil (in particular, <5% by weight), and propellants. Other presentation forms include sticks and blocks. They are produced typically using a gel concentrate comprising essential oils. It is also possible to add formaldehyde (for preservation) and chlorophyll (preferably <5% by weight), and also further ingredients. Air fresheners are not, however, restricted to living spaces, but may also be intended for autos, cupboards, dishwashers, refrigerators or shoes, and even their use in vacuum cleaners is a possibility. In the household (e.g., in cupboards), for example, in addition to the odour improvers, disinfectants as well are employed, containing preferably compounds such as calcium phosphate, talc, stearin, and essential oils, these products taking the form, for example, of sachets.

Consumer product compositions referred to hereinabove, particularly those for use in washing or cleaning applications may contain one or more of the following substances:

Builder substances, surfactants, enzymes, bleaching agents, such as preferably organic and/or inorganic peroxygen compounds, peroxygen activators, water-miscible organic solvents, sequestering agents, electrolytes, pH regulators, thickeners, and further adjuvants such as soil release active substances, optical brighteners, graying inhibitors, color transfer inhibitors, foam regulators, and dyes.

Surfactant include anionic surfactants, nonionic surfactants, and mixtures thereof, but also cationic surfactants, are appropriate. Suitable nonionic surfactants are, in particular, ethoxylation and/or propoxylation products of alkyl glycosides and/or of linear or branched alcohols each having 12 to 18 carbon atoms in the alkyl portion and 3 to 20, by preference 4 to 10, alkyl ether groups. Also usable are corresponding ethoxylation and/or propoxylation products of N-alkylamines, vicinal diols, fatty acid esters and fatty acid amides that correspond, in terms of the alkyl portion, to the aforesaid long-chain alcohol derivatives, and of alkylphenols having 5 to 12 carbon atoms in the alkyl residue.

Suitable anionic surfactants include soaps, and those that contain sulfate or sulfonate groups having preferably alkali ions as cations. Soaps include alkali salts of the saturated or unsaturated fatty acids having 12 to 18 carbon atoms. Such fatty acids can also be used in incompletely neutralized form. Included among the usable surfactants of the sulfate type are the salts of the sulfuric acid semi-esters of fatty alcohols having 12 to 18 carbon atoms, and the sulfated products of the aforesaid nonionic surfactants having a low degree of ethoxylation. Included among the usable surfactants of the sulfonate type are linear alkylbenzenesulfonates having 9 to 14 carbon atoms in the alkyl portion, alkanesulfonates having 12 to 18 carbon atoms, and olefinsulfonates having 12 to 18 carbon atoms that are produced upon reaction of corresponding monoolefins with sulfur trioxide, as well as alpha-sulfofatty acid esters that are produced upon sulfonation of fatty acid methyl or ethyl esters.

Cationic surfactants include esterquats and/or the quaternary ammonium compounds (QACs). QACs may be produced by the reaction of tertiary amines with alkylating agents such as methyl chloride, benzyl chloride, dimethyl sulfate, dodecyl bromide, but also ethylene oxide. The alkylation of tertiary amines having a long alkyl residue and two methyl groups occurs particularly easily, and the quaternization of tertiary amines having two long residues and one methyl group can also be carried out using methyl chloride under mild conditions. Amines that possess three long alkyl residues or hydroxy-substituted alkyl residues have low reactivity, and are quaternized, for example, using dimethyl sulfate. Suitable QACs are, for example, benzalkonium chloride (N-alkyl-N,N-dimethylbenzylammonium chloride), benzalkon B (m,p-dichlorobenzyldimethyl-C12-alkylammonium chloride), benzoxonium chloride (benzyldodecyl-bis(2-hydroxyethypammonium chloride), cetrimonium bromide (N-hexadecyl-N,N-trimethylammonium bromide), benzetonium chloride (N,N-dimethyl-N-[2-[2-[p-(1,1,3,3-tetramethylbutyl)phenoxy]ethoxy]ethyl]benzylammonium chloride), dialkyldimethylammonium chlorides such as di-n-decyldimethylammonium chloride, didecyldimethylammonium bromide, dioctyldimethylammonium chloride, 1-cetylpyridinium chloride, and thiazoline iodide, as well as mixtures thereof. Preferred QACs are the benzalkonium chlorides having $C_8$ to $C_{22}$ alkyl residues, in particular $C_{12}$ to $C_{14}$ alkylbenzyldimethylammonium chloride.

Esterquats include the commercially available methylhydroxyalkyldialkoyloxyalkylammonium methosulfates marketed by the Stepan company under the trademark Stepantex™, or the products of Cognis Deutschland GmbH known under the trade name Dehyquat™, or the Rewoquat™ products of Goldschmidt-Witco.

Surfactants may be employed in amounts of 5 wt % to 50 wt % in a consumer product of the present invention.

Builders include the water-soluble and/or water-insoluble, organic and/or inorganic builders. In particular, they include the water-soluble organic builder substances are polycarboxylic acids, more particularly citric acid and sugar acids, monomeric and polymeric aminopolycarboxylic acids, in particular methylglycinediacetic acid, nitrilotriacetic acid, and ethylenediaminetetraacetic acid, as well as polyaspartic acid, polyphosphonic acids, in particular a minotris(methylenephosphonic acid), ethylenediaminetetrakis(methylenephosphonic acid), and 1-hydroxyethane-1,1-diphosphonic acid, polymeric hydroxy compounds such as dextrin, as well as polymeric (poly)carboxylic acids, polymeric acrylic acids, methacrylic acids, maleic acids, and mixed polymers thereof, which can also contain small proportions of polymerizable substances having no carboxylic-acid functionality. The relative molecular weight of homopolymers of unsaturated carboxylic acids is generally between 5000 and 200,000, that of the copolymers between 2000 and 200,000, based in each case on free acid. Suitable compounds of this class are copolymers of acrylic acid or methacrylic acid with vinyl ethers, such as vinylmethyl ethers, vinyl esters, ethylene, propylene, and styrene, in which the proportion of acid is equal to at least 50 wt %. It is also possible to use, as water-soluble organic builder substances, terpolymers that contain two unsaturated acids and/or salts thereof as monomers and, as a third monomer, vinyl alcohol and/or a vinyl alcohol derivative or a carbohydrate. The first acid monomer or salt thereof may be derived from an ethylenically mono-unsaturated $C_3$ to $C_8$ carboxylic acid. The second acid monomer or salt thereof can be a derivative of a $C_4$ to $C_8$ dicarboxylic acid, for example maleic acid. The third monomeric unit is constituted by vinyl alcohol and/or an esterified vinyl alcohol. Polymers may contain 60 wt % to 95 wt %, in particular 70 wt % to 90 wt %, (meth)acrylic acid or (meth)acrylate, as well as 5 wt % to 40 wt % vinyl alcohol and/or vinyl acetate. Particular polymers are those in which the weight ratio of (meth)acrylic acid respectively (meth) acrylate to maleic acid or maleate is between 1:1 and 4:1. Both the quantities and the weight ratios are based on the acids. The second acid monomer or salt thereof can also be a derivative of an allylsulfonic acid that is substituted in the 2-position with an alkyl radical, e.g. a $C_1$ to $C_4$ alkyl radical, or with an aromatic radical that may be derived from benzene or benzene derivatives. Terpolymers may contain 40 wt to 60 wt %, in particular 45 to 55 wt %, (meth)acrylic acid or (meth)acrylate, particularly preferably acrylic acid or acrylate, 10 wt % to 30 wt %, by preference 15 wt % to 25 wt % methallylsulfonic acid or methallylsulfonate, and as a third monomer 15 wt % to 40 wt %, by preference 20 wt % to 40 wt % of a carbohydrate. This carbohydrate can be, for example, a mono-, di-, oligo-, or poly-saccharide, e.g. sucrose. The terpolymers generally have a relative molecular weight between 1000 and 200,000. Further copolymers include those that comprise, as monomers, acrolein and acrylic acid/acrylic acid salts, or vinyl acetate. Especially for the manufacture of liquid detergents, the organic builder substances can be used in the form of aqueous solutions, for example a 30- to 50-weight-percent aqueous solutions. All the aforesaid acids may be used in the form of their water-soluble salts, in particular their alkali salts.

Organic builder substances can be employed in quantities of up to 40 wt %.

Water-soluble inorganic builder materials include alkali silicates and polyphosphates, e.g. sodium triphosphate. Crystalline or amorphous alkali aluminosilicates, e.g. crystalline sodium aluminosilicates, may also be employed as water-insoluble, water-dispersible inorganic builder materials, in quantities of up to 50 wt %, for example. Aluminosilicates typically comprise particles having a particle size less than 30 μm.

Crystalline alkali silicates may also be employed, either alone or used with amorphous silicates. The alkali silicates usable in consumer products of the present invention as detergency builders may have a molar ratio of alkali oxide to $SiO_2$ below 0.95, in particular from 1:1.1 to 1:12, and can be present in amorphous or crystalline fashion. The alkali silicates may be sodium silicates, in particular the amorphous sodium silicates, having a $Na_2O:SiO_2$ molar ratio from 1:2 to 1:2.8.

Builder substances may be contained in consumer product compositions according to the present invention at levels up to 60 wt %.

Peroxygen compounds include organic peracids or peracid salts of organic acids such as phthalimidopercapronic acid, perbenzoic acid, or salts of diperdodecanedioic acid, hydrogen peroxide, and inorganic salts that release hydrogen peroxide under application conditions, such as perborate, percarbonate, and/or persilicate. If solid peroxygen compounds are to be used, they can be utilized in the form of powders or granulates, which in principle can also be encased in known fashion.

Peroxygen compounds may be employed in amounts up to 50 wt %. The addition of small quantities of known bleaching-agent stabilizers, for example phosphonates, borates respectively metaborates, and metasilicates, as well as magnesium salts such as magnesium sulfate, may be useful.

Compounds that, under perhydrolysis conditions, yield aliphatic peroxocarboxylic acids having preferably 1 to 10 carbon atoms, in particular 2 to 4 carbon atoms, and/or (optionally substituted) perbenzoic acid, can be used as bleach activators. Substances that carry O- and/or N-acyl groups having the aforesaid number of carbon atoms, and/or optionally substituted benzoyl groups, are suitable. Multiple acylated alkylenediamines, in particular tetraacetylethylendiamine (TAED), acylated triazine derivatives, in particular 1,5-diacetyl-2,4-dioxohexahydro-1,3,5-triazine (DADHT), acylated glycolurils, in particular tetraacetyl glycoluril (TAGU), N-acylimides, in particular N-nonanoyl succinimide (NOSI), acylated phenolsulfonates, in particular n-nonanoyl or isononanoyl oxybenzenesulfonate (n- or iso-NOBS), carboxylic acid anhydrides, in particular phthalic acid anhydride, acylated polyvalent alcohols, in particular triacetin, ethylene glycol diacetate, 2,5-diacetoxy-2,5-dihydrofuran, and enol esters, as well as acetylated sorbitol and mannitol respectively mixtures thereof (SORMAN), acylated sugar derivatives, in particular pentaacetylglucose (PAG), pentaacetylfructose, tetraacetylxylose and octaacetyllactose, as well as acetylated, optionally N-alkylated glutamine and gluconolactone, and/or N-acylated lactams, for example N-benzoylcaprolactam, may be employed. Hydrophilically substituted acyl acetates and acyl lactams may likewise be employed. Combinations of conventional bleach activators can also be used. Such bleach activators can be contained in the usual quantity range, by preference in quantities from 1 wt % to 10 wt %, in particular 2 wt % to 8 wt %, based on the entire agent.

In addition to or instead of the aforementioned conventional bleach activators, sulfonimines and/or bleach-intensifying transition metal salts or transition metal complexes can also be contained as bleach catalysts. Included among the appropriate transition metal compounds are, in particular, salen complexes of manganese, iron, cobalt, ruthenium, or molybdenum and nitrogen-analog compounds thereof, carbonyl complexes of manganese, iron, cobalt, ruthenium, or molybdenum, complexes of manganese, iron, cobalt, ruthenium, molybdenum, titanium, vanadium, and copper having nitrogen-containing tripod ligands, amine complexes of cobalt, iron, copper, and ruthenium. Combinations of bleach activators and transition metal bleach catalysts can likewise be used. Bleach-intensifying transition metal complexes, in particular having the central atoms Mn, Fe, Co, Cu, Mo, V, Ti, and/or Ru, can be used in conventional quantities, such as up to 1 wt % based on the weight of the consumer product composition.

Suitable enzymes that may be employed in compositions are those from the class of the proteases, cutinases, amylases, pullulanases, hemicellulases, cellulases, lipases, oxidases, and peroxidases, as well as mixtures thereof. Enzymatically active substances recovered from fungi or bacteria, such as Bacillus subtilis, Bacillus licheniformis, Streptomyces griseus, Humicola lanuginosa, Humicola insolens, Pseudomonas pseudoalcaligenes, or Pseudomonas cepacia, are also suitable. The enzymes that are used as applicable can be adsorbed onto carrier substances and/or embedded into encasing substances in order to protect them from premature inactivation. They may be contained in washing products according to the present invention in amounts typically below 5 wt %.

Optical brighteners include derivatives of diaminostilbenedisulfonic acid or alkali metal salts thereof. Suitable, for example, are salts of 4,4'-bis(2-anilino-4-morpholino-1,3,5-triazinyl-6-amino)stilbene-2,2'-disulfonic acid, or compounds of similar structure that carry, instead of the morpholino group, a diethanolamino group, a methylamino group, an anilino group, or a 2-methoxyethylamino group. Brighteners of the substituted diphenylstyryl type can also be present, e.g. the alkali salts of 4,4'-bis(2-sulfostyryl)diphenyl, of 4,4'-bis(4-chloro-3-sulfostyryl)diphenyl, or of 4-(4-chlorostyryl)-4'-(2-sulfostyryl)diphenyl. Mixtures of the aforesaid optical brighteners can also be used.

Foam inhibitors include organopolysiloxanes and mixtures thereof with microfine, optionally silanated silicic acid, as well as paraffin waxes and mixtures thereof with silanated silicic acid or bis-fatty acid alkylenediamides. Mixtures of different foam inhibitors, for example those made of silicones, paraffins, or waxes, can also be employed. The foam inhibitors, in particular silicone- and/or paraffin-containing foam inhibitors are by preference bound to a granular carrier substance that is soluble or dispersible in water. Mixtures of paraffins and bistearylethylenediamide, in particular may be employed.

Soil release active substances are those compounds that positively influence the ability of oils and fats to be washed out of textiles. This effect becomes particularly apparent when the soiled textile is one that has already been previously washed several times with a washing agent according to the present invention that contains this oil- and fat-releasing component. The preferred oil- and fat-releasing components include, for example, nonionic cellulose ethers such as methyl cellulose and methylhydroxypropyl cellulose having a 15 to 30 wt % proportion of methoxy groups and a 1 to 15 wt % proportion of hydroxypropoxyl groups, based in each case on the nonionic cellulose ethers, as well as polymers, known from the existing art, of phthalic acid and/or terephthalic acid resp. of their derivatives with monomeric and/or polymeric diols, in particular polymers of ethylene terephthalates and/or polyethylene glycol terephthalates or anionically and/or nonionically modified derivatives thereof.

Colour transfer inhibitors include polymers of vinylpyrrolidone, vinylimidazole, vinylpyridine-N-oxide, or copolymers thereof. Also usable are both polyvinylpyrrolidones having molecular weights from 15,000 to 50,000 and polyvinylpyrrolidones having molecular weights above 1,000,000, in particular from 1,500,000 to 4,000,000, N-vinylimidazole/N-vinylpyrrolidone copolymers, polyvinyloxazolidones, copolymers based on vinyl monomers and carboxylic acid amides, pyrrolidone-group-containing polyesters and polyamides, grafted polyamidoamines and polyethylenimines, polymers having amide groups made up of secondary amines, polyamine-N-oxide polymers, polyvinyl alcohols, and copolymers based on acrylamidoalkenyl sulfonic acids. It is also possible, however, to use enzymatic systems encompassing a peroxidase and hydrogen peroxide or a substance that yields hydrogen peroxide in water.

Graying inhibitors are those materials that keep dirt that has been detached from the textile fibers suspended in a washing medium. Water-soluble colloids, usually organic in nature, are suitable for this, for example starch, size, gelatin, salts of ethercarboxylic or ethersulfonic acids of starch or of cellulose, or salts of acid sulfuric acid esters of cellulose or of starch. Water-soluble polyamides containing acid groups are also suitable for this purpose. Starch derivatives other than those recited above can also be used, for example aldehyde starches. Cellulose ethers such as carboxymethyl cellulose (sodium salt), methyl cellulose, hydroxyalkyl cellulose, and mixed ethers such as methylhydroxyethyl cellulose, methylhydroxypropyl cellulose, methylcarboxymethyl cellulose, and mixtures thereof may be used, for example in quantities from 0.1 to 5 wt % based on the weight of the consumer product.

Organic solvents include alcohols having 1 to 4 carbon atoms, in particular methanol, ethanol, isopropanol, and tert-butanol, diols having 2 to 4 carbon atoms, in particular ethylene glycol and propylene glycol, as well as mixtures thereof, and the ethers derivable from the aforesaid compound classes. Water-miscible solvents of this kind are present in washing products according to the present invention in amounts typically not exceeding 30 wt %.

pH regulators include citric acid, acetic acid, tartaric acid, malic acid, lactic acid, glycolic acid, succinic acid, glutaric acid, and/or adipic acid, but also mineral acids, in particular sulfuric acid, or bases, in particular ammonium hydroxides or alkali hydroxides. pH regulators of this kind are contained in the agents according to the present invention in quantities preferably not above 20 wt %, in particular from 1.2 wt % to 17 wt %.

The compounds may be particularly used to perfume household products containing enzymes, such as those defined above, and in particular textile treatment products, such as detergents, containing enzymes.

There now follows a series of examples that serve to further illustrate the invention.

EXAMPLE 1

Synthesis of 3-(3-Isobutyl-5-methylphenyl)propanal (1)

Compound 1 of the present invention was prepared according to Scheme 1.

Scheme 1:

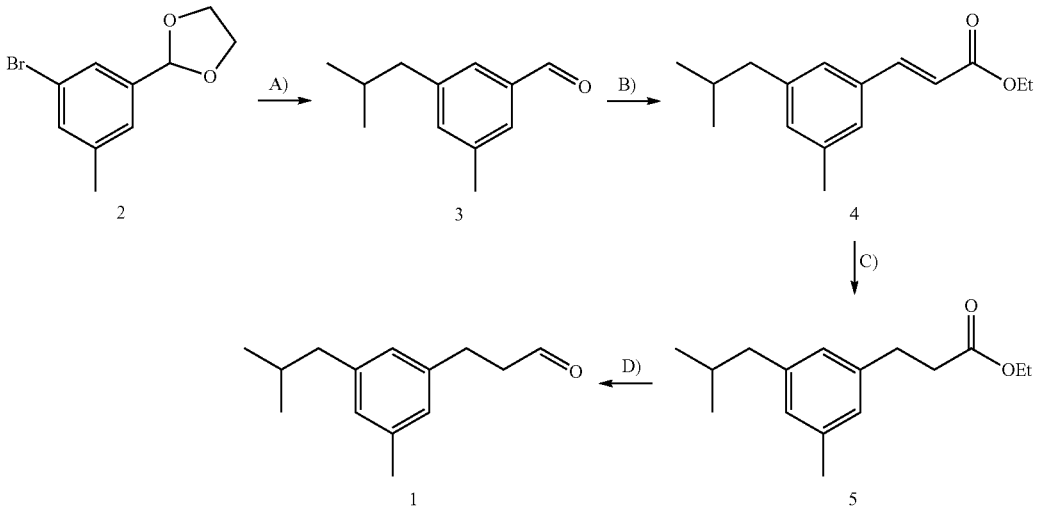

A) Isobutylmagnesiumchloride (2M in THF, 12.0 mL) was added to a suspension of $ZnCl_2$ (2.34 g, 17.2 mmol) in THF (8.5 mL) at 0° C. After the grey-white thick suspension was stirred at 25° C. for 1 h, it was added to a suspension of $[PdCl_2(dppf)].CH_2Cl_2$ (93 mg, 0.11 mmol), CuI (44 mg, 0.23 mmol) and 2-(3-bromo-5-methylphenyl)-1,3-dioxolane (2, 2.78 g, 11.4 mmol) in THF (11.5 mL). The mixture was stirred at 25° C. for 2 h and again for 1 h after addition of 2M aq. HCl (11.5 mL). $H_2O$ was added and the aq. layer was extracted with MTBE (2×). The org. phases were washed with brine, dried ($MgSO_4$), filtered and the filtrate was concentrated. The residue was purified by distillation in the "Kugelrohr" oven (120° C., 0.09 mbar) to yield 1.93 g (96%) of 3-isobutyl-5-methylbenzaldehyde (3) as a colorless oil.

$^1$H NMR ($CDCl_3$, 400 MHz): δ=9.97 (s, 1H), 7.52 (br. s, 1H), 7.47 (br. s, 1H), 7.25-7.23 (m, 1H), 2.52 (d, J=7.3 Hz, 2H), 2.41 (d, J=0.5 Hz, 3H), 1.90 (nonet, J=6.9 Hz, 1H), 0.92 (d, J=6.6 Hz, 6H) ppm.

B) Ethyl 2-(diethoxyphosphoryl)acetate (3.1 mL, 15.4 mmol) was added to a suspension of NaH (50% dispersion in mineral oil, 0.74 g, 15.4 mmol) in THF (8 mL) at 0° C. After the suspension was stirred at 25° C. for 30 min and re-cooled to 0° C., 3-isobutyl-5-methylbenzaldehyde (3, 2.46 g, 14.0 mmol) in THF (7 mL) was added and the mixture was stirred at 25° C. for 5 h. After addition of $H_2O$ at 25° C., the aq. layer was extracted with MTBE (2×). The org. phases were washed with $H_2O$ and brine, dried ($MgSO_4$), filtered and the filtrate was concentrated. The residue was purified by distillation in the "Kugelrohr" oven (130° C., 0.09 mbar) to yield 2.38 g (69%) of (E)-ethyl 3-(3-isobutyl-5-methylphenyl)acrylate (4) as a light yellow oil.

$^1$H NMR ($CDCl_3$, 400 MHz): δ=7.66 (d, J=16.1 Hz, 1H), 7.18 (br. s, 1H), 7.12 (br. s, 1H), 7.00 (br. s, 1H), 6.43 (d, J=16.1 Hz, 1H), 4.27 (q, J=7.1 Hz, 2H), 2.46 (d, J=7.3 Hz, 2H), 2.35 (s, 3H), 1.87 (nonet, J=6.9 Hz, 1H), 1.35 (t, J=7.1 Hz, 3H), 0.92 (d, J=6.6 Hz, 6H) ppm.

C) Pd/C (5% wt, 0.21 g) was added to a solution of (E)-ethyl 3-(3-isobutyl-5-methylphenyl)acrylate (4, 2.11 g, 8.57 mmol) in EtOH (17 mL). The suspension was stirred under $H_2$ (1 atm) at 25° C. for 3 h, filtered through a pad of Celite and washed with hexane. The filtrate was concentrated and the residue was purified by distillation in the "Kugelrohr" oven (130° C., 0.08 mbar) to yield 1.91 g (90%) of ethyl 3-(3-isobutyl-5-methylphenyl)propanoate (5) as a colorless oil having a sweet, fruity, candy odour.

$^1$H NMR ($CDCl_3$, 400 MHz): δ=6.85 (br. s, 1H), 6.82 (br. s, 1H), 6.79 (br. s, 1H), 4.14 (q, J=7.1 Hz, 2H), 2.92-2.88 (m, 2H), 2.63-2.59 (m, 2H), 2.41 (d, J=7.1 Hz, 2H), 2.31 (d,

J=0.5 Hz, 3H), 1.84 (nonet, J=6.9 Hz, 1H), 1.25 (t, J=7.1 Hz, 3H), 0.90 (d, J=6.6 Hz, 6H) ppm.

D) DIBAL-H (1M in $CH_2Cl_2$, 4.0 mL) was added to a solution of ethyl 3-(3-isobutyl-5-methylphenyl)propanoate (5, 1.01 g, 4.03 mmol) in $CH_2Cl_2$ (16 mL) at −78° C. and the mixture was stirred at −78° C. for 3 h. After warming to 0° C., MTBE was added and the reaction was quenched with $H_2O$ (0.2 mL), 3 M aq NaOH (0.2 mL) and $H_2O$ (0.4 mL), and stirred vigorously for 10 min. $MgSO_4$ was added, the mixture was stirred for an additional 10 min and the white solid was removed by filtration. The filtrate was concentrated and the residue was purified by distillation in the "Kugelrohr" oven (120° C., 0.07 mbar) to yield 0.77 g (94%) of 3-(3-isobutyl-5-methylphenyl)propanal (1) as a colorless oil.

$^1$H NMR ($CDCl_3$, 400 MHz): δ=9.83 (t, J=1.6 Hz, 1H), 6.85 (br. s, 1H), 6.84 (br. s, 1H), 6.79-6.77 (m, 1H), 2.91 (t, J=7.5 Hz, 2H), 2.79-2.75 (m, 2H), 2.42 (d, J=7.1 Hz, 2H), 2.31 (d, J=0.7 Hz, 3H), 1.85 (nonet, J=6.9 Hz, 1H), 0.91 (d, J=6.6 Hz, 6H) ppm. $^{13}$C NMR ($CDCl_3$, 100 MHz): δ=201.8 (d), 142.0 (s), 139.9 (s), 137.8 (s), 127.9 (d), 126.4 (d), 126.2 (d), 45.4 (t), 45.3 (t), 30.2 (d), 28.1 (t), 22.4 (2q), 21.3 (q) ppm. MS (EI): m/z (%)=204 ($M^{+\bullet}$, 23), 176 (9), 161 (12), 148 (18), 133 (53), 119 (100), 105 (44), 91 (33), 77 (12), 43 (14), 41 (19), 29 (9).

Odour description: green aldehydic, citrus juicy orange

EXAMPLE 2

Synthesis of (E)-3-(2-isobutyl-4-methylphenyl) Acrylaldehyde (6) and 3-(2-isobutyl-4-methylphenyl)propanal (7)

Compounds 6 and 7 were prepared in four or five steps, respectively, according to Scheme 2.

Scheme 2:

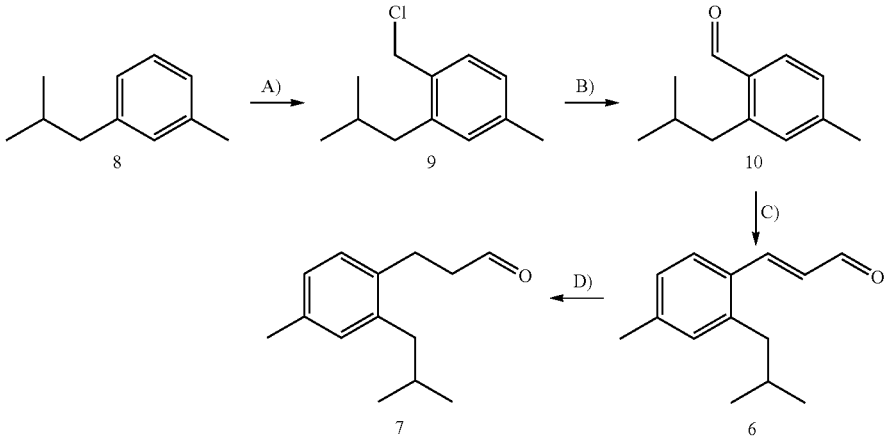

A) A mixture of $ZnCl_2$ (53.9 g, 395 mmol), 1-isobutyl-3-methylbenzene (8, 293 g, 1.98 mol), paraformaldehyde (66.3 g, 2.21 mol) and AcOH (230 mL) under Ar was warmed gently to 40° C. Hydrogen chloride gas was bubbled into the reaction solution during 2 h at 40° C. until consumption of 1-isobutyl-3-methylbenzene completed. The reaction mixture was cooled to 25° C. $H_2O$ was added, and the reaction mixture was extracted with MTBE (3×). The comb. org. layers were washed with $H_2O$ (5×), sat. aq. $NaHCO_3$ solution and brine. The org. layer was dried ($MgSO_4$), filtered and concentrated. The crude product was distilled under vacuum to give a colorless liquid (275 g, 70% yield) which was a mixture of 1-(chloromethyl)-2-isobutyl-4-methylbenzene (9) and 1-(chloromethyl)-4-isobutyl-2-methylbenzene in a ratio of 22:78.

1-(Chloromethyl)-2-isobutyl-4-methylbenzene: $^1$NMR ($CDCl_3$, 300 MHz): δ=7.20 (d, J=7.4 Hz, 1H), 7.02 (d, J=7.4 Hz, 1H), 6.98 (s, 1H), 4.60 (s, 2H), 2.57 (d, J=7.6 Hz, 2H), 2.32 (s, 3H), 1.96-1.81 (m, 1H), 0.95 (d, J=6.6 Hz, 6H) ppm.

1-(Chloromethyl)-4-isobutyl-2-methylbenzene: $^1$H NMR ($CDCl_3$, 300 MHz): δ=7.20 (d, J=7.4 Hz, 1H), 7.02 (d, J=7.4 Hz, 1H), 6.98 (s, 1H), 4.60 (s, 2H), 2.43 (d, J=7.4 Hz, 2H), 2.40 (s, 3H), 1.89-1.79 (m, 1H), 0.90 (d, J=6.6 Hz, 6H) ppm.

B) A mixture of 1-(chloromethyl)-2-isobutyl-4-methylbenzene (9) and 1-(chloromethyl)-4-isobutyl-2-methylbenzene (273 g, 1.39 mol, in ratio of 22:78), hexamethylenetetramine (Urotropine, 292 g, 2.08 mmol), and AcOH (120 g, 2.00 mol) in EtOH (300 mL) and $H_2O$ (200 mL) under Ar was refluxed for 10 h. The reaction was cooled to 25° C., and the org. phase was separated. The aq. phase was extracted with MTBE (3×). The comb. org. layers were washed with $H_2O$ (3×), sat. aq. $NaHCO_3$ solution and brine. The org. layer was dried ($MgSO_4$), filtered and concentrated. The crude product was distilled under vacuum to give a colorless liquid (180 g) which was a mixture of 2-isobutyl-4-methylbenzaldehyde and 4-isobutyl-2-methylbenzaldehyde in ratio of 22:78. The product was further fractional distilled to give pure 2-isobutyl-4-methylbenzaldehyde (10, 15.0 g, 6% yield) and 4-isobutyl-2-methylbenzaldehyde (95.0 g, 39% yield).

2-Isobutyl-4-methylbenzaldehyde: Boiling point: 98-101° C./0.15 mbar; $^1$H NMR ($CDCl_3$, 300 MHz): δ=10.22 (s, 1H), 7.73 (d, J=7.8 Hz, 1H), 7.14 (d, J=7.8 Hz, 1H), 7.02 (s, 1H), 2.85 (d, J=7.1 Hz, 2H), 2.38 (s, 3H), 1.92-1.77 (m, 1H), 0.93 (d, J=6.6 Hz, 6H) ppm.

Odour description: green leathery, spicy saffron

4-Isobutyl-2-methylbenzaldehyde: Boiling point: 102-108° C./0.15 mbar; $^1$H NMR ($CDCl_3$, 300 MHz): δ=10.20 (s, 1H), 7.70 (d, J=7.8 Hz, 1H), 7.13 (d, J=7.8 Hz, 1H), 7.03 (s, 1H), 2.64 (s, 3H), 2.49 (d, J=7.2 Hz, 2H), 1.99-1.81 (m, 1H), 0.91 (d, J=6.6 Hz, 6H) ppm.

Odour description: weak, green aromatic, thyme origanum, resinous, slightly isobutyl benzoate;

C) To a mixture of 2-isobutyl-4-methylbenzaldehyde (10, 11.0 g, 62.4 mmol) and boron trifluoride etherate (0.044 g, 0.31 mmol) under Ar, trimethoxymethane (7.95 g, 74.9 mmol) was added dropwise over 33 min at 25° C. After completion of the addition, the reaction was stirred for 20 min at 25° C. Ethoxyethene (5.40 g, 74.9 mmol) was added dropwise over 20 min at 30-35° C. and the reaction was stirred for 30 min. $NaHCO_3$ (1.0 g) and $H_2O$ (0.50 mL) were added with stirring over 2 min, then stirring was stopped. The clean solution was decanted, and methanesulfonic acid (0.090 g, 0.94 mmol) in $H_2O$ (5.0 ml) was added. The reaction mixture was heated to reflux and volatiles were distilled off until the pot temperature reached 105° C. The reaction was cooled to 90° C. and toluene (40 ml) was added. The resulting mixture was washed successively with aq. solution of $H_2SO_4$ (63%), brine and $H_2O$. The org. layer was dried ($MgSO_4$), filtered and concentrated. The crude product was purified by column chromatography followed by Kugelrohr distillation to give (E)-3-(2-isobutyl-4-methylphenyl)acrylaldehyde (6, 7.50 g, 59% yield) as a colorless liquid.

Boiling point: 145-150° C./0.15 mbar. $^1H$ NMR ($CDCl_3$, 300 MHz): δ=9.70 (d, J=7.7 Hz, 1H), 7.76 (d, J=15.7 Hz, 1H), 7.53 (d, J=8.0 Hz, 1H), 7.06 (d, J=8.0 Hz, 1H), 7.02 (s, 1H), 6.64 (dd, J=15.7, 7.7 Hz, 1H), 2.62 (d, J=7.2 Hz, 2H), 2.36 (s, 3H), 1.88-1.77 (m, 1H), 0.93 (d, J=6.6 Hz, 6H) ppm. $^{13}C$ NMR ($CDCl_3$, 75 MHz): δ=193.9 (d), 150.5 (d), 141.9 (s), 141.2 (s), 132.2 (d), 129.8 (s), 128.5 (d), 127.5 (d), 126.8 (d), 42.3 (t), 30.7 (d), 22.4 (q), 22.4 (q), 21.5 (q) ppm. MS: m/z (%)=77 (3), 91 (13), 105 (3), 115 (20), 131 (23), 145 (100), 159 (20), 171 (2), 187 (3), 202 (6) [$M^+$].

Odour description: green, floral.

D) A mixture of Pd/C (5% wt, 0.30 g), sodium acetate (2.00 g, 24.4 mmol) and (E)-3-(2-isobutyl-4-methyl phenyl) acrylaldehyde (6, 7.00 g, 34.6 mmol) in EtOAc (35 mL) was stirred under $H_2$ (1 atm) at 25° C. overnight. The reaction mixture was filtered through a pad of $SiO_2$ and washed with MTBE. The filtrate was concentrated. The crude product was purified by column chromatography followed by Kugelrohr distillation to give 3-(2-isobutyl-4-methylphenyl)propanal (7, 3.50 g, 17.1 mmol, 50% yield, purity >99%) as a colorless liquid.

Boiling point: 145-150° C./0.15 mbar. $^1H$ NMR ($CDCl_3$, 300 MHz): δ=9.83 (s, 1H), 7.02 (d, J=7.7 Hz, 1H), 6.95 (d, J=7.7 Hz, 1H), 6.94 (s, 1H), 2.92 (t, J=7.7 Hz, 2H), 2.71 (t, J=7.7 Hz, 2H), 2.45 (d, J=7.2 Hz, 2H), 2.29 (s, 3H), 1.91-1.77 (m, 1H), 0.93 (d, J=6.5 Hz, 6H) ppm. $^{13}C$ NMR ($CDCl_3$, 75 MHz): δ=201.8 (d), 139.3 (s), 135.6 (s), 135.2 (s), 131.1 (d), 128.7 (d), 126.9 (d), 45.2 (t), 41.9 (t), 29.9 (d), 24.4 (t), 22.6 (q), 22.6 (q), 21.0 (q) ppm. MS: m/z (%)=77 (6), 91 (15), 105 (18), 119 (100), 133 (12), 143 (28), 161 (30), 171 (2), 186 (10), 204 (5) [$M^+$].

Odour description: green floral, animalic costus.

EXAMPLE 3

Synthesis of 2-(2-isobutyl-4-methylphenyl)propanal (11)

Compound 11 was prepared in two steps according to Scheme 3.

Scheme 3:

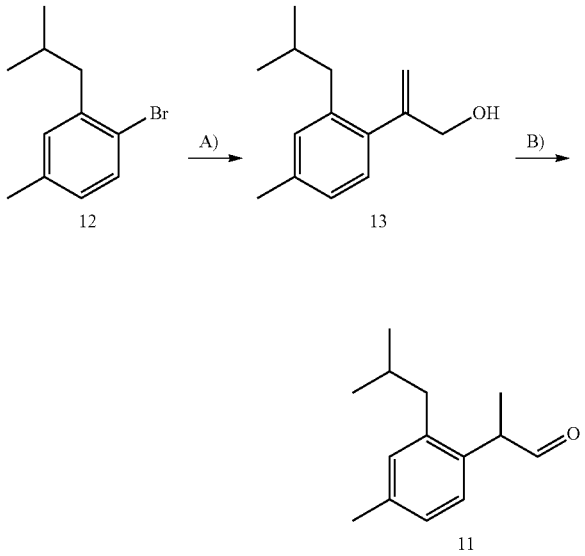

A) 1-Bromo-2-isobutyl-4-methylbenzene (12, 182 g, 0.80 mol, 75%) in $Et_2O$ (550 ml) was added to Mg (22.4 g, 0.92 mol) in $Et_2O$ (50 ml) to form the Grignard reagent. CuI (9.06 g, 48.1 mmol) was added at 25° C. and the mixture stirred for 40 min. Propargyl alcohol (18.0 g, 0.32 mol) in $Et_2O$ (100 ml) was added dropwise over 30 min, maintaining the temperature below 30° C. Following reflux for 80 min, the mixture was stirred overnight and then quenched into sat. aq. $NH_4Cl$ (400 ml) and iced $H_2O$ (400 ml). The aq. phase was extracted with $Et_2O$ (2×) and the comb. org. phases were washed with $H_2O$ (2×, to pH 6-7). The org. phase was dried ($MgSO_4$), filtered and evaporated down to yield crude 2-(2-isobutyl-4-methylphenyl)prop-2-en-1-ol (13, 126 g) which was purified by fractionation through a vigreux column, collecting fractions boiling at 108-111° C. at 0.07 mbar (25.5 g, 39% yield).

B) 2-(4-Isobutyl-2-methylphenyl)prop-2-en-1-ol (13, 11.9 g, 58.3 mmol) was dissolved in $CH_2Cl_2$ (500 ml) under Ar. $CBr_4$ (5.17 g, 15.6 mmol) and $PPh_3$ (4.09 g, 15.6 mmol) were jointly added portionwise to control the temperature below 25° C. After stirring for 125 h, the mixture was quenched with iced water and the aq. phase was extracted with $CH_2Cl_2$. The org. phase was washed with $H_2O$, dried ($MgSO_4$), filtered and the solvent evaporated to yield a crude product (18.2 g). The crude product was purified by Kugelrohr distillation (115° C., 0.07 mbar) followed by flash chromatography on $SiO_2$, eluting with hexane/MTBE, yielding 2-(2-isobutyl-4-methylphenyl)propanal (11, 3.40 g, 29% yield, purity 93%).

$^1H$ NMR ($CDCl_3$, 400 MHz): δ=9.64 (d, J=1.0 Hz, 1H), 7.03 (dd, J=7.8, 1.2 Hz, 1H), 7.01 (br. s, 1H), 6.91 (d, J=7.8 Hz, 1H), 3.84 (qd, J=6.9, 1.0 Hz, 1H), 2.57-2.46 (m, 2H), 2.32 (s, 3H), 1.82 (nonet, J=6.9 Hz, 1H), 1.37 (d, J=6.9 Hz, 3H), 0.95 (d, J=6.6 Hz, 3H), 0.95 (d, J=6.6 Hz, 3H) ppm. $^{13}C$ NMR (CDCl3, 100 MHz): δ=201.4 (d), 140.0 (s), 136.7 (s), 133.2 (s), 131.9 (d), 127.8 (d), 127.5 (d), 48.2 (d), 42.2 (t), 30.3 (d), 22.5 (q), 22.5 (q), 21.1 (q), 15.5 (q) ppm. MS: m/z (%)=55 (20), 77 (5), 91 (14), 105 (14), 115 (15), 119 (21), 133 (100), 161 (9), 175 (39), 204 (12) [$M^+$].

EXAMPLE 4

2-(4-isobutyl-2-methylphenyl)propanal (14)

14

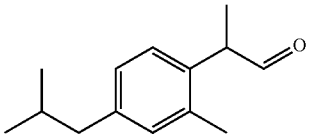

1-Bromo-4-isobutyl-2-methylbenzene was converted according to the procedure described in example 3 via 2-(2-isobutyl-4-methylphenyl)prop-2-en-1-ol to 2-(4-isobutyl-2-methylphenyl)propanal (14).

$^{1}$H NMR ($CDCl_3$, 400 MHz): δ=9.64 (d, J=1.2 Hz, 1H), 7.01 (br. s, 1H), 7.00 (dd, J=7.8, 1.7 Hz, 1H), 6.95 (d, J=7.6 Hz, 1H), 3.80 (qd, J=7.1, 1.2 Hz, 1H), 2.43 (d, J=7.3 Hz, 2H), 2.33 (s, 3H), 1.85 (nonet, J=6.9 Hz, 1H), 1.39 (d, J=7.1 Hz, 3H), 0.92 (d, J=6.6 Hz, 6H) ppm. $^{13}$C NMR ($CDCl_3$, 100 MHz): δ=201.3 (d), 141.0 (s), 136.3 (s), 133.5 (s), 131.8 (d), 127.4 (d), 127.3 (d), 49.0 (d), 45.0 (t), 30.2 (d), 22.4 (q), 22.4 (q), 19.7 (q) 14.3 (q) ppm. MS: m/z (%)=57 (12), 77 (5), 91 (14), 105 (14), 117 (17), 133 (26), 175 (100), 204 (9) [$M^+$].

EXAMPLE 5

In Vitro Metabolism Study

A comparison of compounds of the present invention and Lilial™.

Cryopreserved hepatocytes from male rats (Sprague Dawley; Lifetechnologies) were defrozen, washed in Cyropreserved Hepatocytes Recovery Medium (CHRM; Lifetechnologies) and suspended in Williams E Medium (WEM; Lifetechnologies). Lilial™, or the compounds of the present invention (final concentration: 100 μM) were added to the cells (1×106 viable cells/ml) and suspensions were incubated up to 4 hours at 37° C. on a shaker in duplicate. Metabolism of testosterone was monitored as positive control. Decrease of the test compounds and formation of the corresponding benzoic acid derivative was determined by GC-MS analysis of methyl esters formed after derivatisation with trimethylsilyl diazomethane (Sigma-Aldrich) in methanol. The test compounds react with diazomethane yielding a methyl ketone which was used for the quantification of Lilial™ and the compound of formula (I). Metabolism was stopped with ice cold 1 M HCl, samples were extracted with tert-butyl methyl ether (MTBE) and analysed by GC-MS. Incubations containing testosterone as control were also stopped with ice cold 1 M HCl, centrifuged to separate the cells, filtrated and the decrease of testosterone analysed by LC-MS. To quantify decrease of the test substances and formation of benzoic acid metabolites, calibration curves of reference materials (Lilial™ and the compounds of the present invention, tert-butyl benzoic acid (Fluka) was prepared in hepatocyte incubation medium and analysed like the hepatocyte samples.

A rapid decrease of testosterone as positive control was observed indicating that the hepatocytes were metabolically active. The compounds of the present invention and Lilial™ were metabolised rapidly in rat hepatocytes and no residual compound except for 2% with one compound was measured after 4 h. Whereas tert-butyl benzoic acid was detected as metabolite of Lilial™ (3.4-3.9 μM) no benzoic acid derivatives were formed from compounds of the present invention (Table 1). Limit of detection was <1 μM.

Table 1 (below), shows the concentrations of Lilial™ and compounds of the present invention as well as corresponding benzoic acid metabolites in rat hepatocytes within 4 hours incubation. Initial test concentration at 0 hours incubation was 100 μM.

It is clear from the data presented in Table 1 that the ortho or meta substituent at the benzene ring of the compounds of the present invention does affect the formation of the corresponding benzoic acid derivative in vitro. Since benzoic acid derivatives such as tert-butyl benzoic acid from Lilial™ cause reproductive toxicity in male rats, these toxic effects in male rats are prevented by the ortho-substituent and are reduced by the meta-substituent of the compounds of the present invention.

TABLE 1

| Test compound | Residual conc. (μM) | Benzoic acid derivative | concentration (μM) |
|---|---|---|---|
| 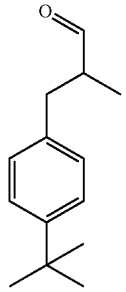 | 0 | 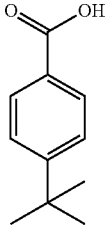 | 3.5-3.9 |
| 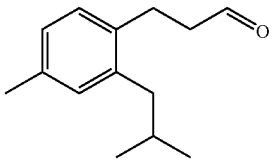 | 0 | 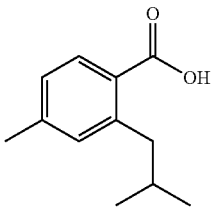 | not found |

TABLE 1-continued

| Test compound | Residual conc. (μM) | Benzoic acid derivative | concentration (μM) |
|---|---|---|---|
| 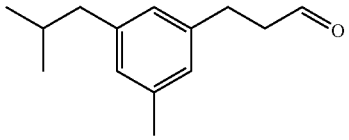 | 1.5 | 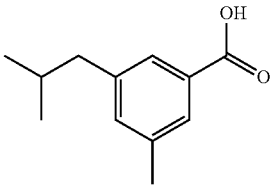 | 0.7-1.0 |

The invention claimed is:

1. [A compound according to formula 1

Formula 1

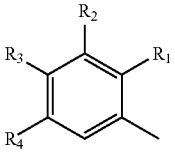

wherein $R_1$ is H;

$R_2$ is H, or when $R_1$ and $R_3$ is H, then $R_2$ is $CHR_5CHR_6CHO$, $CR_5{=}CR_6CHO$ or $C(CH_3)CHO$, wherein $R_5$, $R_6$ each independently may represent H or methyl;

$R_3$ is H, or when $R_1$ and $R_2$ is H, then $R_3$ is $CHR_5CHR_6CHO$, $CR_5{=}CR_6CHO$ or $C(CH_3)CHO$, wherein $R_5$, $R_6$ each independently may represent H or methyl;

and $R_4$ is a branched or linear, saturated or unsaturated, unsubstituted or substituted residue, or a $C_2$-$C_7$ alkyl or alkenyl residue]*The compound, 3-(2-isobutyl-4-methylphenyl)propanal.*

2. [The compound according to claim 1 which is a perfume ingredient] *A pro-perfume which releases the compound, 3-(2-isobutyl-4-methylphenyl)propanal.*

[3. The compound of claim 2, which exhibits green odour characteristics.]

[4. A pro-perfume, which releases the compound represented by the formula 1

Formula 1

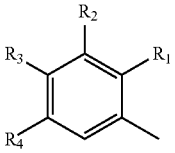

wherein $R_1$ is H;

$R_2$ is H, or when $R_1$ and $R_3$ is H, then $R_2$ is $CHR_5CHR_6CHO$, $CR_5{=}CR_6CHO$ or $C(CH_3)CHO$, wherein $R_5$, $R_6$ each independently may represent H or methyl;

$R_3$ is H, or when $R_1$ and $R_2$ is H, then $R_3$ is $CHR_5CHR_6CHO$, $CR_5{=}CR_6CHO$ or $C(CH_3)CHO$, wherein $R_5$, $R_6$ each independently may represent H or methyl; and $R_4$ is a branched or linear, saturated or unsaturated, unsubstituted or substituted residue, $C_2$-$C_7$ alkyl or alkenyl residue.]

[5. The pro-perfume of claim 4, which is an imine, aminal, hemi-aminal or enamine of the compound according to formula I.]

[6. The pro-perfume of claim 4 which is a perfume ingredient.]

[7. The pro-perfume of claim 6 which exhibits green odor characteristics.]

[8. A perfume composition comprising the pro-perfume of claim 4.]

[9. A personal care or household care composition comprising at least a pro-perfume as defined in claim 4.]

[10. A method of imparting muguet odour characteristics to a fine fragrance or consumer product comprising the step of adding thereto a pro-perfume as defined in claim 4 and, selectively excluding from said fine fragrance or consumer product any aryl-substituted alkanal compounds, which are unsubstituted on the ring at the position ortho to the substituent containing aldehyde functionality, said selective addition or exclusion being based on the susceptibility of said compounds to enzymatically-mediated degradation to their benzoic acid derivatives when incubated with hepatocytes isolated from rats, said compounds being suitable for addition on the basis that they do not degrade to their benzoic acid derivatives, whereas said compounds being excluded on the basis that they do degrade to their benzoic acid derivatives.]

[11. A perfume composition comprising a compound according to claim 1.]

[12. A perfume composition according to claim 11 that is substantially free of any aryl-substituted propanal odourants, that are unsubstituted on the aryl ring at a position ortho to the substituent bearing the aldehyde functionality.]

[13. A perfume composition according to claim 11 comprising one or more additional fragrance ingredients.]

[14. A perfume composition according to claim 13 which comprises 3-(4-isobutyl-2-methylphenyl)propanal.]

[15. A personal care or household care composition comprising at least a perfume composition according to claim 11.]

[16. A perfume composition according to claim 11 that is substantially free of LILIAL.]

[17. A personal care or household care composition comprising at least a compound as defined in claim 1.]

[18. A personal care or household care composition according to claim 17, further comprising enzymes.]

[19. A personal or household care composition according to claim 17, which is a textile treatment product.]

[20. A personal or household care composition according to claim 17 which is a detergent composition.]

21. A method of imparting muguet odour characteristics to a fine fragrance or consumer product comprising the step of adding thereto [a compound as defined in] *the compound of* claim 1 and, selectively excluding from said fine fragrance or consumer product any aryl-substituted alkanal compounds, which are unsubstituted on the ring at the position ortho to the substituent containing aldehyde functionality, said selective addition or exclusion being based on the susceptibility of said compounds to enzymatically-mediated degradation to their benzoic acid derivatives when incubated with hepatocytes isolated from rats, said compounds being suitable for addition on the basis that they do not degrade to their benzoic acid derivatives, whereas said compounds being excluded on the basis that they do degrade to their benzoic acid derivatives.

*22. The compound of claim 1, which exhibits green odour characteristics.*

*23. A perfume composition comprising the compound of claim 1.*

*24. The perfume composition of claim 23 which is substantially free of any aryl-substituted propanal odourants, that are unsubstituted on the aryl ring at a position ortho to the substituent bearing the aldehyde functionality.*

*25. A perfume composition according to claim 23 comprising one or more additional fragrance ingredients.*

*26. A personal care or household care composition comprising the compound of claim 1.*

*27. A personal care or household care composition comprising a perfume composition of claim 23.*

*28. A personal care or household care composition of claim 26, further comprising an enzyme.*

*29. A personal care or household care composition of claim 26, which is a textile treatment product.*

*30. A personal care or household care composition of claim 26, which is a detergent composition.*

*31. The perfume composition of claim 25 which comprises 3-(4-isobutyl-2-methylphenyl)propanal.*

*32. The pro-perfume of claim 2, which is an imine, aminal, hemi-aminal or enamine of 3-(2-isobutyl-4-methylphenyl)propanal.*

*33. The pro-perfume of claim 32 which releases a compound which exhibits green odor characteristics.*

*34. A perfume composition comprising the pro-perfume of claim 2.*

*35. A personal care or household care composition comprising the pro-perfume of claim 2.*

*36. A method of imparting muguet odour characteristics to a fine fragrance or consumer product comprising the step of adding thereto the pro-perfume of claim 2 and, selectively excluding from said fine fragrance or consumer product any aryl-substituted alkanal compounds, which are unsubstituted on the ring at the position ortho to the substituent containing aldehyde functionality, said selective addition or exclusion being based on the susceptibility of said compounds to enzymatically-mediated degradation to their benzoic acid derivatives when incubated with hepatocytes isolated from rats, said compounds being suitable for addition on the basis that they do not degrade to their benzoic acid derivatives, whereas said compounds being excluded on the basis that they do degrade to their benzoic acid derivatives.*

*37. A perfume composition according to claim 23 that is substantially free of 3-(4-tert-butylphenyl)-2-methylpropanal.*

* * * * *